US007662820B2

(12) United States Patent
Moheno et al.

(10) Patent No.: US 7,662,820 B2
(45) Date of Patent: Feb. 16, 2010

(54) DIPTERINYL CALCIUM PENTAHYDRATE (DCP) AND THERAPEUTIC METHODS BASED THEREON

(75) Inventors: Phillip Moheno, La Jolla, CA (US); Wolfgang Pfleiderer, Constance (DE)

(73) Assignee: SanRX Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 11/981,398

(22) Filed: Oct. 30, 2007

(65) Prior Publication Data

US 2008/0166355 A1 Jul. 10, 2008

Related U.S. Application Data (60) Provisional application No. 60/863,547, filed on Oct. 30, 2006.

(51) Int. Cl.
| | |
|---|---|
| C07D 475/04 | (2006.01) |
| A61K 31/4985 | (2006.01) |
| C07F 3/02 | (2006.01) |
| C07F 3/04 | (2006.01) |
| C07F 3/06 | (2006.01) |
| C07F 3/08 | (2006.01) |
| C07F 1/08 | (2006.01) |
| C07F 7/02 | (2006.01) |
| C07F 7/22 | (2006.01) |
| C07F 15/02 | (2006.01) |
| A61P 35/00 | (2006.01) |

(52) U.S. Cl. .................. 514/249; 544/257; 544/225
(58) Field of Classification Search ................. 514/249; 544/225, 226, 257
See application file for complete search history.

(56) References Cited

U.S. PATENT DOCUMENTS

| 6,358,953 B1 | 3/2002 | Moheno |
| 6,844,343 B1 | 1/2005 | Pfleiderer et al. |

OTHER PUBLICATIONS

Mitsumi, et al., Molecular Crystals & Liquid Crystals Science & Technology, Section A: Molecular Crystals & Liquid Crystals (1996), 276, 229-235.*
Cameron, D.A. et al., "Tamoxifen induced apoptosis in ZR-75 breast cancer xenografts antedates tumour regression," Breast Cancer Res. Treat. 45(20:99-107 (1997).
Emi, M. et al., "Targeted therapy against Bcl-2-related proteins in breast cancer cells," Breast Cancer Res. 7(6):R940-R952 (2005).
Han, G.Z. et al., "Synergism between the anticancer actions of 2-methoxyestradiol and microtubule-disrupting agents in human breast cancer," Cancer Res. 65(2):387-393 (2005).
Hoke, E.M. et al., "Desferal inhibits breast tumor growth and does not interfere with the tumoricidal activity of doxorubicin," Free Radic. Biol. Med. 39(3):403-411 (2005).
Jones, L.W., "Effects of exercise training on antitumor efficacy of doxorubicin in MDA-MB-231 breast cancer xenografts," Clin. Cancer Res. 11(18):6695-6698 (2005).
Jordan, V.C. et al., "Immune-deficient animals to study "hormone-dependent" breast and endometrial cancer," J. Steroid Biochem. 34(1-6):169-176 (1989).
Kokolis et al., "Pteridine and Riboflavin in Tumor Tissue and the Effect of Chloramphenicol and Isoxanthopterin," Z. Naturforsch. B27:292-295 (1972).
LaMontagne, K.R. et al., "Recombinant epoetins do not stimulate tumor growth in erythropoietin receptor-positive breast carcinoma models," Mol. Cancer Ther. 5(2):347-355 (2006).
Lewisohn et al., "The Action of Xanthopterin on Tumor Growth," Proc. Soc. Exp. Biol. Med. 56:144-145 (1944).
Liao, Y. et al., "Enhanced paclitaxel cytotoxicity and prolonged animal survival rate by a nonviral-mediated systemic delivery of E1A gene in orthotopic xenograft human breast cancer," Cancer Gene Ther. 11(9):594-602 (2004).
Mewani, R.R. et al., "Enhanced therapeutic effects of doxorubicin and paclitaxel in combination with liposome-entrapped ends-modified raf antisense oligonucleotide against human prostate, lung and breast tumor models," Int. J. Oncol. 24(5):1181-1188 (2004).
Milacic, V. et al., "A novel anticancer gold(III) dithiocarbamate compound inhibits the activity of a purified 20S proteasome and 26S proteasome in human breast cancer cell cultures and xenografts," Cancer Res. 66(21):10478-10486 (2006).
Robinson, S.P. et al., "Preclinical studies with toremifene as an antitumor agent," Breast Cancer Res. Treat. 16 (Suppl):S9-S17 (1990).
Robinson, S.P. et al., "Antiestrogenic action of toremifene on hormone-dependent,—independent, and heterogeneous breast tumor growth in the athymic mouse," Cancer Res. 49(7):1758-1762 (1989).
Sweeney, C.J. et al., "The sesquiterpene lactone parthenolide in combination with docetaxel reduces metastasis and improves survival in a xenograft model of breast cancer," Mol. Cancer Ther. 4(6):1004-1012 (2005).
Taras, T.L., et al., "In vitro and in vivo biologic effects of Ospemifene (FC-1271a) in breast cancer," J. Steroid Biochem. Mol. Biol. 77(4-5):271-279 (2001).
Warnberg, F. et al., "Effect of a farnesyl transferase inhibitor (R115777) on ductal carcinoma in situ of the breast in a human xenograft model and on breast and ovarian cancer cell growth in vitro and in vivo," Breast Cancer Res. 8(2):R21-R31 (2006), Epub Apr. 12, 2006.
Winkler et al., "Calcium-pterin suppresses mitogen-induced tryptophan degradation and neopterin production in peripheral blood mononuclear cells," Immunobiology 211:779-784 (2006).
Woessner, R. et al., "Comparison of three approaches to doxorubicin therapy: free doxorubicin, liposomal doxorubicin, and beta-glucuronidase-activated prodrug (HMR 1826)," Anticancer Res. 20(4):2289-2296 (2000).

(Continued)

Primary Examiner—Mark L Berch
Assistant Examiner—Cecilia M Jaisle
(74) Attorney, Agent, or Firm—Wilson Sonsini Goodrich & Rosati (57) ABSTRACT

Provided herein is dipterinyl calcium pentahydrate (DCP) and therapeutic methods based thereon. Also provided herein is the compound dipterinyl calcium pentahydrate (DCP) or an analog or polymorph thereof.

3 Claims, 10 Drawing Sheets

OTHER PUBLICATIONS

Yamamoto, D. et al., "Synergistic effects induced by cycloprodigiosin hydrochloride and epirubicin on human breast cancer cells," Breast Cancer Res. Treat. 72(10):1-10 (2002).

Yen, W.C. et al., "The selective retinoid X receptor agonistbexarotene (LGD1069, Targretin) prevents and overcomes multidrug resistance in advanced breast carcinoma," Mol. Cancer Ther. 4(5):824-834 (2005).

Crispini, A. et al., "Hdrogen-bonding network in metal-pterin complexes: Synthesis and characterization of water-soluble octahedral nickel and cadmium pterine derivatives," Crystal Growth & Design 5(4):1597-1601 (2005).

Mitsumi, M. et al., "Metal-pteridine complexes having three-dimensional hydrogen-bonded networks," Inorg. Chem. 34(12):3367-3370 (1995).

PCT/US07/23012 Search Report dated Jun. 17, 2008.

Moheno, P., et al., "Plasma Cytokine Changes Induced by the Antitumor Agents Dipterinyl Calcium Pentahydrate (DCP) and Related Calcium Pterins," Immunology, article in press, received Apr. 2, 2008.

Moheno, P., et al., "Plasma Cytokine Changes Induced by the Antitumor Agents Dipterinyl Calcium Pentahydrate (DCP) and Related Calcium Pterins," Pteridines 19 (2):49 (2008).

Moheno, P., et al., "Cytokine and IDO Metabolite Changes Effected by Calcium Pterin During Inhibition of MDA-MB-231 Xenograph Tumors in Nude Mice," International Journal of Pharmaceutics 355:238-248 (2008).

Moheno, P., et al., "Mechanism of Action Studies with the Antitumor Agent Calcium-Pterin," Pteridines 18(2):50 (2007).

Moheno, P., et al., "Role of Calcium Pterin in Natural Killer (NK) Cell Activation and Indoleamine 2,3-Dioxygenase (IDO) Modulation for Antitumor Activity," Pteridines 16:140 (2005).

Moheno, P., et al., "Calcium Pterin as an Antitumor Agent," International Journal of Pharmaceutics 271:293-300 (2004).

Winkler, C., et al., "Calcium-Pterin Suppresses Mitogen-Induced Tryptophan Degradation and Neopterin Production in Peripheral Blood Mononuclear Cells," Immunobiology 211:779-784 (2006).

Stea, B., et al., "Folate and Pterin Metabolism by Cancer Cells in Culture," Cancer Research 38:2378-2384 (1978).

* cited by examiner

Figure 2. Structure of DCP as determined by single crystal x-ray diffraction

Figure 3. Nude mice treated with DCP showed no significant weight loss

Figure 4: Determination of optimum dose in nude mice

Figure 5: Comparison of DCP to other forms of calcium pterin after 46 days of treatment Figure 6: Comparison of DCP to other forms of calcium pterin after 57 days of treatment Figure 7: Treatment/Control (T/C) values in nude mice w/ MDA-MB-231 after 11 days of treatment Figure 8: Treatment/Control (T/C) values in nude mice w/ MDA-MB-231 after 36 days of treatment Figure 9: Treatment/Control (T/C) values in nude mice w/ MDA-MB-231 after 47 days of treatment

US 7,662,820 B2

DIPTERINYL CALCIUM PENTAHYDRATE (DCP) AND THERAPEUTIC METHODS BASED THEREON

RELATED APPLICATIONS

This application claims priority to U.S. Provisional Application No. 60/863,547, filed on Oct. 30, 2006, which is incorporated by reference in its entirety.

SUMMARY OF THE INVENTION

One embodiment provides dipterinyl calcium pentahydrate (DCP) and therapeutic methods based thereon. Another embodiment provides the compound dipterinyl calcium pentahydrate (DCP) or an analog or polymorph thereof. Another embodiment provides a method of synthesizing dipterinyl calcium pentahydrate (DCP) comprising: dissolving pterin in an aqueous solution of NaOH, adding $CaCl_2.2H_2O$ to the solution with stirring at a pH of about 11, continuing stirring for about 1 day, and collecting the precipitate as DCP. One embodiment provides a method of modulating tryptophan production comprising administering to a subject an effective amount of DCP. Another embodiment provides a method of modulating tryptophan production comprising administering to a subject an effective amount of DCP suspension. Additional embodiments provide a method of modulating tryptophan degradation comprising administering to a subject an effective amount of DCP. Another embodiment provides method of modulating tryptophan degradation comprising administering to a subject an effective amount of DCP suspension. Another embodiment provides a method of modulating neopterin production comprising administering to a subject an effective amount of DCP. An additional embodiment provides a method of modulating neopterin production comprising administering to a subject an effective amount of DCP suspension.

Yet another embodiment provides a method of modulating IFN-γ production comprising administering to a subject an effective amount of DCP. An additional embodiment provides a method of modulating IFN-γ production comprising administering to a subject an effective amount of DCP suspension. One embodiment provides a method of modulating the activity of the enzyme IDO comprising administering to a subject an effective amount of DCP. Another embodiment provides a method of modulating the activity of the enzyme IDO comprising administering to a subject an effective amount of DCP suspension. One embodiment provides a method of modulating oxidants production comprising administering to a subject an effective amount of DCP. Another embodiment provides a method of modulating oxidants production comprising administering to a subject an effective amount of DCP suspension. Yet another embodiment provides a method of modulating free radical production comprising administering to a subject an effective amount of DCP. An additional embodiment provides a method of modulating free radical production comprising administering to a subject an effective amount of DCP suspension One embodiment provides a method of modulating release of reactive oxygen species (ROS) comprising administering to a subject an effective amount of DCP. Another embodiment provides a method of modulating release of reactive oxygen species (ROS) comprising administering to a subject an effective amount of DCP suspension. An additional embodiment provides a method of modulating release pro-inflammatory transcription factor NF-κB comprising administering to a subject an effective amount of DCP. A further embodiment provides a method of modulating release pro-inflammatory transcription factor NF-κB comprising administering to a subject an effective amount of DCP suspension. Another embodiment provides a method of modulating the expression of down-stream genes for a cytokine, a chemokine, adhesion molecule, growth factor, enzyme and/or immune receptor comprising administering to a subject an effective amount of DCP. An additional embodiment provides a method of modulating the expression of down-stream genes for a cytokine, a chemokine, adhesion molecule, growth factor, enzyme and/or immune receptor comprising administering to a subject an effective amount of DCP suspension. Another embodiment provides a method of reducing inflammatory activity in a subject comprising administering to a subject an effective amount of DCP. A further embodiment provides a method of reducing inflammatory activity in a subject comprising administering to a subject an effective amount of DCP suspension. Yet another embodiment provides a method of reducing or suppressing expression of the enzyme IDO comprising administering to a subject an effective amount of DCP. Another embodiment provides a method of reducing or suppressing expression of the enzyme IDO comprising administering to a subject an effective amount of DCP suspension. One embodiment provides a method of modulating human T-cell response comprising administering to a subject an effective amount of DCP. Another embodiment provides a method of modulating human T-cell response comprising administering to a subject an effective amount of DCP suspension.

One embodiment provides a method of reducing or suppressing allogeneic immune tolerance comprising administering to a subject an effective amount of DCP. Another embodiment provides a method of reducing or suppressing allogeneic immune tolerance comprising administering to a subject an effective amount of DCP suspension. Another embodiment provides a method of modulating immune resistance in human solid tumors comprising administering to a subject an effective amount of DCP. Another embodiment provides a method of modulating immune resistance in human solid tumors comprising administering to a subject an effective amount of DCP suspension. Another embodiment provides a method of modulating antiproliferative activity comprising administering to a subject an effective amount of DCP. Another embodiment provides a method of modulating antiproliferative activity comprising administering to a subject an effective amount of DCP suspension.

One embodiment provides a compound of formula (I):

$$M(pterin)_x(H_2O)_y$$

wherein:
M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;
X is an integer from 1 to 8; and
y is an integer of from 1 to 8.

Another embodiment provides a method of inhibiting tumor cells in an animal comprising the administration of a therapeutically effective amount of a compound of formula (I):

$$M(pterin)_x(H_2O)_y$$

wherein:
M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;

X is an integer from 1 to 8; and
y is an integer of from 1 to 8.

One embodiment provides a method of treating a viral infection comprising the administration of a therapeutically effective amount of a compound of formula (I):

wherein:

M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$;

X is an integer from 1 to 8; and
y is an integer of from 1 to 8.

Another embodiment provides a pharmaceutical composition comprising a pharmaceutically acceptable excipient and a compound of formula (I):

wherein:

M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^2+$, $Pt^{2+}$, $Si^{2+}$, and $Sm^{2+}$;

X is an integer from 1 to 8; and
y is an integer of from 1 to 8.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

Glossary

To more readily facilitate an understanding of the invention and its embodiments, the meanings of terms used herein will become apparent from the context of this specification in view of common usage of various terms and the explicit definitions of other terms provided in the glossary below or in the ensuing description.

As used herein, the terms "comprising," "including," and "such as" are used in their open, non-limiting sense.

The use of the term "about" in the present disclosure means "approximately," and illustratively, the use of the term "about" indicates that values slightly outside the cited values may also be effective and safe, and such dosages are also encompassed by the scope of the present claims.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Carrier materials" include any commonly used excipients in pharmaceutics and should be selected on the basis of compatibility with the active pharmaceutical ingredient and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

The term "controlled release" includes any non-immediate release formulation, including but not limited to entericcoated formulations and sustained release, delayed-release and pulsatile release formulations.

The term "delayed-release" includes any non-immediate release formulation, including but not limited to, film-coated formulations, enteric-coated formulations, encapsulated formulations, sustained release formulations and pulsatile release formulations.

"Diffusion facilitators" and "dispersing agents" include materials that control the diffusion of an aqueous fluid through a coating. Exemplary diffusion facilitators/dispersing agents include, e.g., hydrophilic polymers, electrolytes, Tween® 60 or 80, PEG and the like. Combinations of one or more erosion facilitator with one or more diffusion facilitator can also be used in the present invention.

"Diluents" increase bulk of the composition to facilitate compression. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinized starch; compressible sugar, such as Di-Pac® (Amstar); mannitol; hydroxypropylmethylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; mannitol; sodium chloride; inositol; bentonite; and the like.

"Filling agents" include compounds such as lactose, calcium carbonate, calcium phosphate, dibasic calcium phosphate, calcium sulfate, microcrystalline cellulose, cellulose powder, dextrose; dextrates; dextran, starches, pregelatinized starch, sucrose, xylitol, lactitol, mannitol, sorbitol, sodium chloride, polyethylene glycol, and the like. The terms "therapeutically effective amount" and "effective amount" in relation to the amount of active pharmaceutical ingredient mean, consistent with considerations known in the art, the amount of active pharmaceutical ingredient effective to elicit a pharmacologic effect or therapeutic effect without undue adverse side effects.

An "enteric-coating" is a substance that remains substantially intact in the stomach but dissolves and releases at least some of the drug once reaching the small intestine. Generally, the enteric-coating comprises a polymeric material that prevents release in the low pH environment of the stomach but that ionizes at a slightly higher pH, typically a pH of 4 or 5, and thus dissolves sufficiently in the small intestines to gradually release the active agent therein.

The term "immediate release" is intended to refer to any formulation in which all or part of the active pharmaceutical ingredient is in solution either before administration or immediately (i.e., within about 30 minutes) after administration. For example, with an "immediate release" formulation, oral administration results in immediate release of the agent from the composition into gastric fluid. For delayed-release formulations, the opposite is generally true, the rate of release of drug from the dosage form is the rate-limiting step in the delivery of the drug to the target area.

"Lubricants" are compounds which prevent, reduce or inhibit adhesion or friction of materials. Exemplary lubricants include, e.g., stearic acid; calcium hydroxide; talc; sodium stearyl fumerate; a hydrocarbon such as mineral oil, or hydrogenated vegetable oil such as hydrogenated soybean oil (Sterotex®); higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol or a methoxypolyethylene glycol such as Carbowax™, sodium oleate, glyceryl behenate, polyethylene glycol, magnesium or sodium lauryl sulfate, colloidal silica such as Syloid™, Carb-O-Sil®, a starch such as corn starch, silicone oil, a surfactant, and the like.

The term "pharmaceutically acceptable" is used adjectivally herein to mean that the modified noun is appropriate for use in a pharmaceutical product.

"Solubilizers" include compounds such as citric acid, succinic acid, fumaric acid, malic acid, tartaric acid, maleic acid, glutaric acid, sodium bicarbonate, sodium carbonate and the like.

"Stabilizers" include compounds such as any antioxidation agents, buffers, acids, and the like.

"Suspending agents" or "thickening agents" include compounds such as polyvinylpyrrolidone, e.g., polyvinylpyrrolidone K12, polyvinylpyrrolidone K17, polyvinylpyrrolidone K25, or polyvinylpyrrolidone K30; polyethylene glycol, e.g., the polyethylene glycol can have a molecular weight of about 300 to about 6000, or about 3350 to about 4000, or about 7000 to about 5400; sodium carboxymethylcellulose; methylcellulose; hydroxypropylmethylcellulose; polysorbate-80; hydroxyethylcellulose; sodium alginate; gums, such as, e.g., gum tragacanth and gum acacia; guar gum; xanthans, including xanthan gum; sugars; cellulosics, such as, e.g., sodium carboxymethylcellulose, methylcellulose, sodium carboxymethylcellulose, hydroxypropylmethylcellulose, hydroxyethylcellulose; polysorbate-80; sodium alginate; polyethoxylated sorbitan monolaurate; polyethoxylated sorbitan monolaurate; povidone and the like.

"Surfactants" include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF); and the like.

As used herein, the terms "suspension" and "solution" are interchangeable with each other and generally mean a solution and/or suspension of the substituted benzimidazole in an aqueous medium.

The term "sustained release" is used in its conventional sense to refer to a drug formulation that provides for gradual release of a drug over an extended period of time, and, may sometimes, although not necessarily, result in substantially constant blood levels of a drug over an extended time period.

The term "treat" or "treatment" as used herein refers to any treatment of a disorder or disease associated with gastrointestinal disorder, and includes, but is not limited to, preventing the disorder or disease from occurring in a mammal which may be predisposed to the disorder or disease, but has not yet been diagnosed as having the disorder or disease; inhibiting the disorder or disease, for example, arresting the development of the disorder or disease; relieving the disorder or disease, for example, causing regression of the disorder or disease; or relieving the condition caused by the disease or disorder, for example, stopping the symptoms of the disease or disorder.

Pterin has been a point of interest in the biomedical research community for some time. Xanthopterin was found to inhibit sarcoma growth in mice over 60 years ago (Lewisohn et al, *Proc. Soc. Exp. Biol. Med.* (1944) 56, 144-145). Isoxanthopterin was also shown to inhibit tumor growth (Kokolis et al, *Z. Naturforsch.* (1972) B27, 292-95). The National Cancer Institute subsequently tested xanthopterin, isoxanthopterin and pterin but obtained inconsistent results (Drug Evaluation Branch, Developmental Therapeutics Program, Division of Cancer Treatment, National Cancer Institute, Bethesda, Md. 1957, 1958, 1959, 1960, 1964, 1969, 1971, 1972, 1973, 1974, 1975, 1977. NSC 41836, 91557, 118090, 11540, 18696, 170929). In 1996, Moheno disclosed the strong antitumor efficacy of a 2:1 (w/w) xanthopterin/isoxanthopterin suspension in female C3H/HeOuJ mice (U.S. Pat. No. 5,534,514).

Pterin

Further investigations by Moheno demonstrated the importance of selecting an immunocompotent mouse strain for the evaluation of anti-tumor efficacy of pterin and related analogs (Moheno, *Int. J. Pharm.* (2004), 271, 293-300). In this study, a suspension of calcium pterin in the molar ratio of 1:4/calcium:pterin (known as CaPterin) was found to possess significant antitumor efficacy against MDA-MB-231 human breast xenographs in nude mice, as well as highly significant activity against spontaneous mammary gland tumors in C3H/HeN-MTV+ mice, based upon National Cancer Institute standards. Immunomodulatory action for CaPterin was deduced by comparing the antitumor efficacy of CaPterin in four different mouse/tumor systems: i.e., the two cited above, as well as Balb/c mice with EMT6 xenographs and SCID mice with MDA-MB-231 xenographs. Comparison of results obtained by testing CaPterin in either nude or SCID mice (severely compromised immunodeficient) implanted with MDA-MB-231 human cancer cells showed a significant antitumor response in the nudes and no response in the SCIDs. This comparison argues for B-cell immunological involvement in the mechanism of CaPterin antitumor activity since nude mice possess B-cell capability while SCID mice do not. This comparison also indicates that there is no measurable direct cancer cell toxicity from the CaPterin. Results showing no CaPterin antitumor efficacy against EMT6 tumor cells implanted in Balb/c mice also suggest an antitumor mechanism involving B-cells, since transforming growth factor beta (TGF-beta), produced by EMT6 cells, is known to cause B-cell apoptosis. These results indicate that CaPterin's antitumor mechanism involves antibody-dependent cellular cytotoxicity (ADCC) mediated, for example, by natural killer (NK) cells, interlukin-2.

Further study of the immunomodulatory properties of CaPterin was performed by Moheno and co-workers (Winkler et al, Immunobiology.(2006) 211, 779-84). They found that CaPterin was able to suppress both the activity of IDO, the degradation of tryptophan and the production of neopterin in PHA- and Con A-stimulated PBMC in a dose-dependent manner. In PHA- and Con A-stimulated PBMC, the production of IFN-γ is increased and induces the degradation of tryptophan and the production of neopterin. Accelerated tryptophan degradation and high IDO expression levels have been associated with poor prognosis in cancer patients.

Provided herein is dipterinyl calcium pentahydrate (DCP), which is suitable as an antitumor agent. Antitumor dose-response data are presented for dipterinyl calcium pentahydrate (DCP) at two dosages.

Therapeutically effective amounts of dipterinyl calcium pentahydrate may be administered as the aqueous suspension. As well, it is contemplated to administer DCP as the active ingredient in a pharmaceutical composition. Accordingly, provided herein are pharmaceutical compositions, which include therapeutically effective amounts of dipterinyl calcium pentahydrate and one or more pharmaceutically acceptable carriers, diluents, or excipients. The carrier(s), diluent(s) or excipient(s) must be acceptable in the sense of being compatible with the other ingredients of the formulation and not deleterious to the recipient thereof. According to another aspect of the invention there is also provided a process for the preparation of a pharmaceutical formulation including admixing dipterinyl calcium pentahydrate with one or more pharmaceutically acceptable carriers, diluents or excipients.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

One embodiment provides dipterinyl calcium pentahydrate (DCP) or a polymorph thereof. Another embodiment is a method of synthesizing dipterinyl calcium pentahydrate (DCP) comprising dissolving pterin in an aqueous solution of NaOH, adding CaCl2.2H2O to the solution with stirring at a pH of about 11, continuing stirring for about 1 day and collecting the precipitate as DCP.

In another embodiment is a method of modulating tryptophan production comprising administering to a subject an effective amount of DCP. In yet another embodiment is a method of modulating tryptophan production comprising administering to a subject an effective amount of DCP suspension. In another embodiment is a method of modulating tryptophan degradation comprising administering to a subject an effective amount of DCP. A further embodiment is a method of modulating tryptophan degradation comprising administering to a subject an effective amount of DCP suspension.

In one embodiment is a method of modulating neopterin production comprising administering to a subject an effective amount of DCP. In a further embodiment is a method of modulating neopterin production comprising administering to a subject an effective amount of DCP suspension.

In an additional embodiment is a method of modulating IFN-γ production comprising administering to a subject an effective amount of DCP. In yet another embodiment is a method of modulating IFN-γ production comprising administering to a subject an effective amount of DCP suspension.

In one embodiment is a method of modulating the activity of the enzyme IDO comprising administering to a subject an effective amount of DCP. In another embodiment is a method of modulating the activity of the enzyme IDO comprising administering to a subject an effective amount of DCP suspension.

In one embodiment is a method of modulating oxidants production comprising administering to a subject an effective amount of DCP. In yet another embodiment is a method of modulating oxidants production comprising administering to a subject an effective amount of DCP suspension.

In one embodiment is a method of modulating free radical production comprising administering to a subject an effective amount of DCP. In a further embodiment is a method of modulating free radical production comprising administering to a subject an effective amount of DCP suspension. In another embodiment is a method of modulating release of reactive oxygen species (ROS) comprising administering to a subject an effective amount of DCP. In yet another embodiment is a method of modulating release of reactive oxygen species (ROS) comprising administering to a subject an effective amount of DCP suspension.

In one embodiment is a method of modulating release pro-inflammatory transcription factor NF-κB comprising administering to a subject an effective amount of DCP. In another embodiment is a method of modulating release pro-inflammatory transcription factor NF-κB comprising administering to a subject an effective amount of DCP suspension.

In another embodiment is a method of modulating the expression of down-stream genes for a cytokine, a chemokine, adhesion molecule, growth factor, enzyme and/or immune receptor comprising administering to a subject an effective amount of DCP. In a further embodiment is a method of modulating the expression of down-stream genes for a cytokine, a chemokine, adhesion molecule, growth factor, enzyme and/or immune receptor comprising administering to a subject an effective amount of DCP suspension.

In another embodiment is a method of reducing inflammatory activity in a subject comprising administering to a subject an effective amount of DCP. In still another embodiment is a method of reducing inflammatory activity in a subject comprising administering to a subject an effective amount of DCP suspension.

In another embodiment is a method of reducing or suppressing expression of the enzyme IDO comprising administering to a subject an effective amount of DCP. In a further embodiment is a method of reducing or suppressing expression of the enzyme IDO comprising administering to a subject an effective amount of DCP suspension.

In another embodiment is a method of modulating human T-cell response comprising administering to a subject an effective amount of DCP. In an additional embodiment is a method of modulating human T-cell response comprising administering to a subject an effective amount of DCP suspension.

In another embodiment is a method of reducing or suppressing allogeneic immune tolerance comprising administering to a subject an effective amount of DCP. In yet another embodiment is a method of reducing or suppressing allogeneic immune tolerance comprising administering to a subject an effective amount of DCP suspension.

In another embodiment is a method of modulating immune resistance in human solid tumors comprising administering to a subject an effective amount of DCP. In an additional embodiment is a method of modulating immune resistance in human solid tumors comprising administering to a subject an effective amount of DCP suspension.

In another embodiment is a method of modulating antiproliferative activity comprising administering to a subject an effective amount of DCP. In still another embodiment is a method of modulating antiproliferative activity comprising administering to a subject an effective amount of DCP suspension.

In another aspect of the invention is the compound of formula (I): $M(pterin)_x(H2O)_y$ wherein: M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$; X is an integer from 1 to 8; and y is an integer of from 1 to 8. In another embodiment is a method of inhibiting tumor cells in an animal comprising the administration of a therapeutically effective amount of a compound of formula (I): $M(pterin)_x(H2O)_y$, wherein: M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$; X is an integer from 1 to 8; and y is an integer of from 1 to 8.

In another embodiment is a method of treating a viral infection comprising the administration of a therapeutically effective amount of a compound of formula (I): $M(pterin)_x(H2O)_y$ wherein: M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$; X is an integer from 1 to 8; and y is an integer of from 1 to 8.

In another embodiment is a pharmaceutical composition comprising a pharmaceutically acceptable excipient and a compound of formula (I): $M(pterin)_x(H2O)_y$, wherein: M is a bivalent metal ion selected from the group consisting of $Ca^{2+}$, $Cu^{2+}$, $Mg^{2+}$, $V^{2+}$, $Cr^{2+}$, $Mn^{2+}$, $Fe^{2+}$, $Mo^{2+}$, $Zn^{2+}$, $Sr^{2+}$, $Ba^{2+}$, $Ra^{2+}$, $Ru^{2+}$, $Rh^{2+}$, $Pd^{2+}$, $Cd^{2+}$, $Sn^{2+}$, $W^{2+}$, $Re^{2+}$, $Os^{2+}$, $Ir^{2+}$, $Pt^{2+}$, $Si^{2+}$, and $Sm^{2+}$; X is an integer from 1 to 8; and y is an integer of from 1 to 8.

EXAMPLES

Example 1

Synthesis of Dipterinyl Calcium Pentahydrate (DCP)

Pure pterin (81.7 mg, 0.5 mmol) was dissolved in $H_2O$ (50 ml) and 0.1 N NaOH (6 ml) and $CaCl_2 \cdot 2H_2O$ (36.7 mg, 0.25 mmol) was added to the clear solution with stirring (pH 10.93). A yellowish precipitate was formed within a few minutes. Stirring was continued for 1 day and then the precipitate collected and dried in a vacuum desiccator to give 75 mg. The elemental analysis is consistent with $(C_6H_4N_5O)_2Ca \cdot 5H_2O$ (MW 454.4).

| | | | |
|---|---|---|---|
| Calculated: | C: 31.74 | H: 4.00 | N: 30.85 |
| Found: | C: 31.22 | H: 3.97 | N: 29.83. |

The comparison of the extinctions of the UV spectra of pterin and $(C_6H_4N_5O)_2Ca \cdot 5H_2O$ taken at pH 13 show the following:

| | |
|---|---|
| Pterin: | 223 nm (8,700), 250 nm (21,380), 357 nm (8,510) |
| $(C_6H_4N_5O)_2Ca \cdot 5H_2O$: | 223 nm (14,450), 250 nm (39,810), 357 nm (13,490) |

Figure 2:
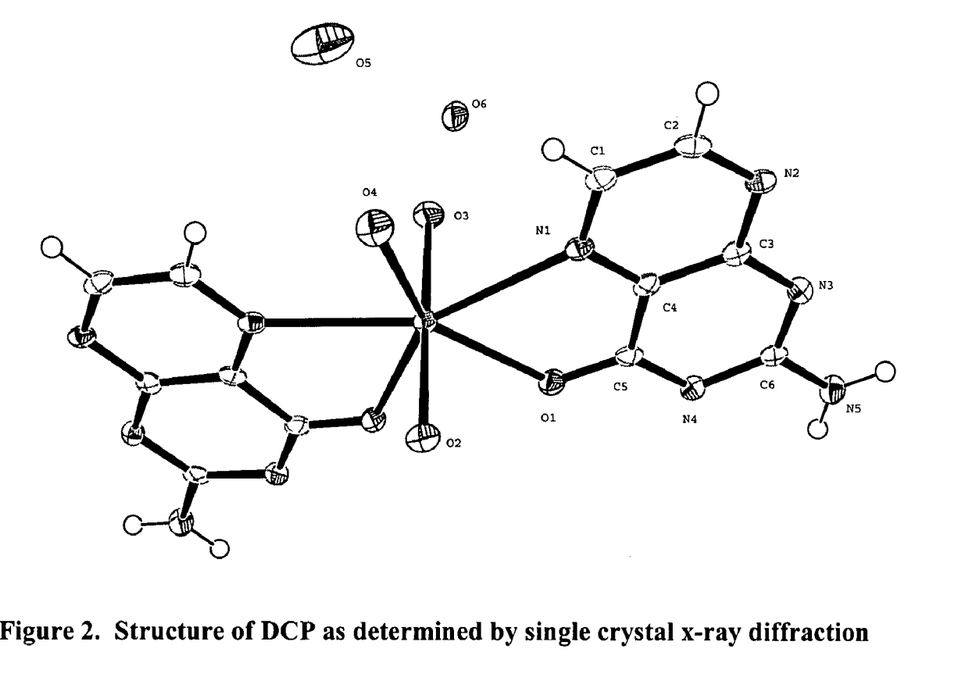
FIG. 2: Structure of DCP as determined by single crystal X-ray diffraction.

The structure of DCP as determined by single crystal x-ray diffraction is shown in FIG. 2.

Dipterinyl calcium pentahydrate (DCP) suspensions:
A 1.1 mg/ml suspension was prepared by mixing 44 mg dipterinyl calcium pentahydrate in 40 ml distilled $H_2O$. A 3.3 mg/ml suspension was prepared by mixing 132 mg dipterinyl calcium pentahydrate in 40 ml distilled $H_2O$.

Example 2

In Vivo Testing

Cell Line Propagation and Inoculation: The MDA-MB-231 human breast tumor cell lines were supplied by SRI International (Menlo Park, Calif.) and propagated using standard in vitro cell expansion methods. Briefly, cells were grown in L-15 media from Gibco (Cat. No. 11415-064) supplemented with 2 mM L-Glutamine and 10% Fetal Bovine Serum (FBS). The cells were cultured in an incubator with 5% C02, 37.50C, and 80% humidity. Cells were harvested with 0.25% (w/v) Trypsin-0.03% (w/v) EDTA solution. Cells were prepared for injection by standard methods to appropriate concentrations. Animals were temporarily restrained but not anesthetized for the inoculation of the tumor cells. Animals were subcutaneously injected with the tumor cells in a 100-200 µl volume.

Animal Care: The animals were housed 4 to a cage in approved micro-isolator cages. Caging bedding and related items were autoclaved prior to use. No other species were housed in the same room(s) as the experimental animals. The rooms were well ventilated (greater than 10 air changes per hour) with 100% fresh air (no air recirculation). A 12-hour light/12-hour dark photoperiod was maintained, except when room lights were turned on during the dark cycle to accommodate study procedures. Room temperature was maintained between 16-22° C. Animal room and cage cleaning was performed according to Perry Scientific SOP (Standard Operating Procedure). Animals had ad libitum access to irradiated ProLab mouse chow. Autoclaved and chlorinated, municipal tap water was available ad libitum to each animal via water bottles. Treatment of the animals was in accordance with Perry Scientific SOP, which adhered to the regulations outlined in the USDA Animal Welfare Act (9 CFR, Parts 1, 2 and 3) and the conditions specified in The Guide for Care and Use of Laboratory Animals (ILAR publication, 1996, National Academy Press). The protocol was approved by Perry Scientific's Institutional Animal Care and Use Committee prior to initiation of the study. The study conduct was in general compliance with the US FDA Good Laboratory Practice Regulations currently in effect (21 CFR, Part 58).

Antitumor efficacy was evaluated in nude mice with MDA-MB-231 human tumor xenografts by Perry Scientific (San Diego, Calif.). Twenty-nine athymic nude were each injected subcutaneously with 10×106 MDA-MB-231 cancer cells into the right flank. When tumors reached 3-5 mm in size, the mice were divided into five treatment groups of five each and a control group of four mice. Four of these with outlying tumor sizes or non-tumor takes were excluded shortly after treatment began: one each from the (1:4 mol:mol) calcium pterin group, the (1:2 mol:mol) calcium pterin group, the DCP (69 mg/kg/day) group, and one from the control group. Experimental groups were treated by oral gavage once daily with the indicated test suspensions or solutions. Control groups were untreated. Daily dosing was for 7 days per week. Animals were restrained but not anesthetized for oral dosing. Tumors were measured twice weekly with calipers and body weights taken twice weekly on the day of tumor measurements. Blood was collected from all animals via cardiac puncture at termination (after 70 to 98 days of treatment) and processed to EDTA plasma for analysis.

Tumor Growth Rate Measurements: Each animal was individually tracked for tumor growth by external caliper measurements of protruding tumor. Primary tumor sizes were measured using calipers and an approximate tumor volume calculated using the formula 1/2 (a×b2), where b was the smaller of two perpendicular diameters.

For each group, the mean and standard error of the mean (SEM) of the ratio V/Vo, Relative Tumor Volume (RTV), were plotted as a function of treatment time after inoculation. V0 was the tumor volume at Day 0, when treatment began. Time course statistical analyses based upon repeated measures ANOVA models were used (StatView SE+Graphics, v 1.03).

Results

Figure 1A:
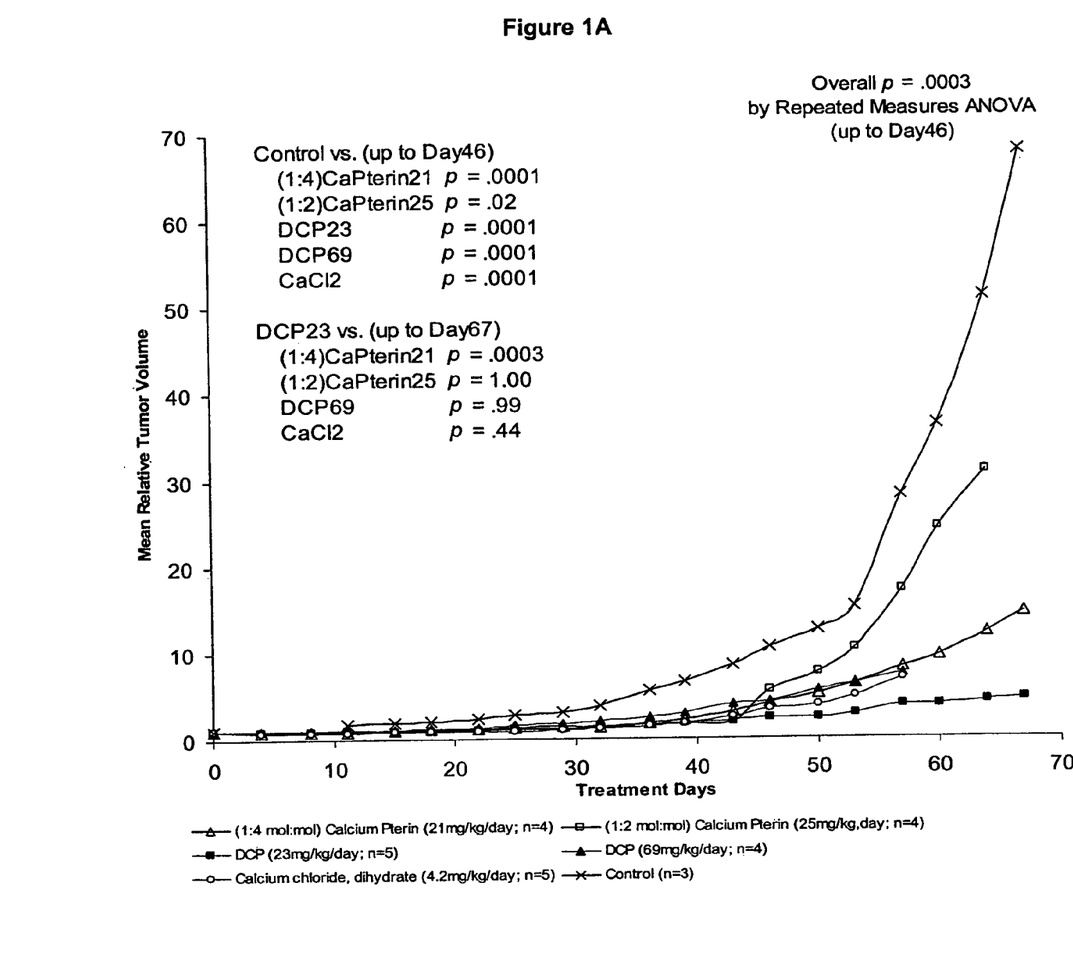
FIGS. 1A and 1B (with SEMs): Twenty-nine athymic nude (nu/nu) female mice, ages 3-4 weeks, were inoculated with 10×106 MDA-MB-231 cancer cells subcutaneously into the right flank of each mouse. When tumors reached 3-5 mm in size, twenty-five of the mice were divided into five treatment groups of five mice each. Four mice were assigned as controls. Four mice with outlying tumor sizes or non-tumor takes were subsequently excluded. Experimental groups were treated by oral gavage once daily with the indicated test suspensions or solution. The control group was untreated.
Figure 1B:
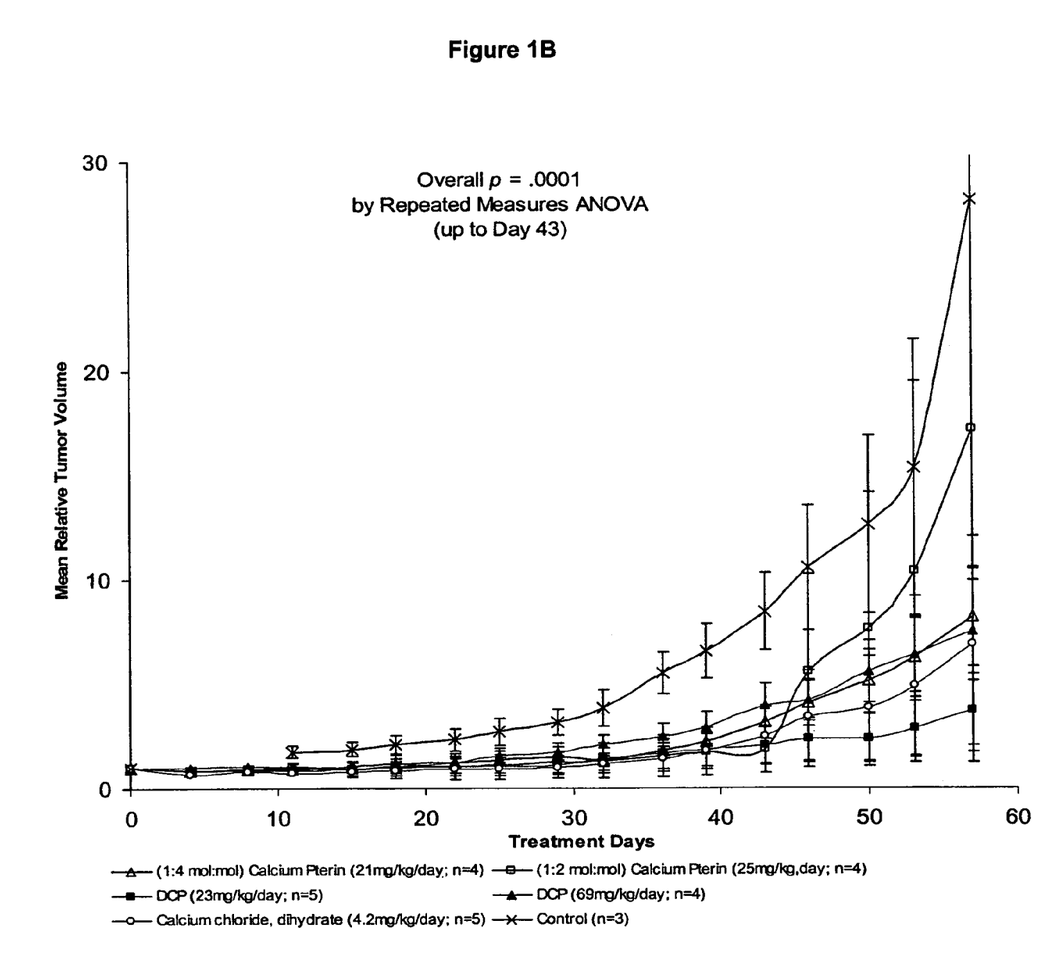

FIG. 1 shows that calcium pterin (1:4 mol:mol form), dipterinyl calcium pentahydrate (DCP) at both dosages tested, and calcium chloride dihydrate all significantly inhibit MDA-MB-231 xenograph growth in nude mice. These findings identify a new efficacious form of calcium pterin, dipterinyl calcium pentahydrate (DCP). Tumor size data for the control group at days 4 and 7 were missed due to a technical oversight.

Figure 3:
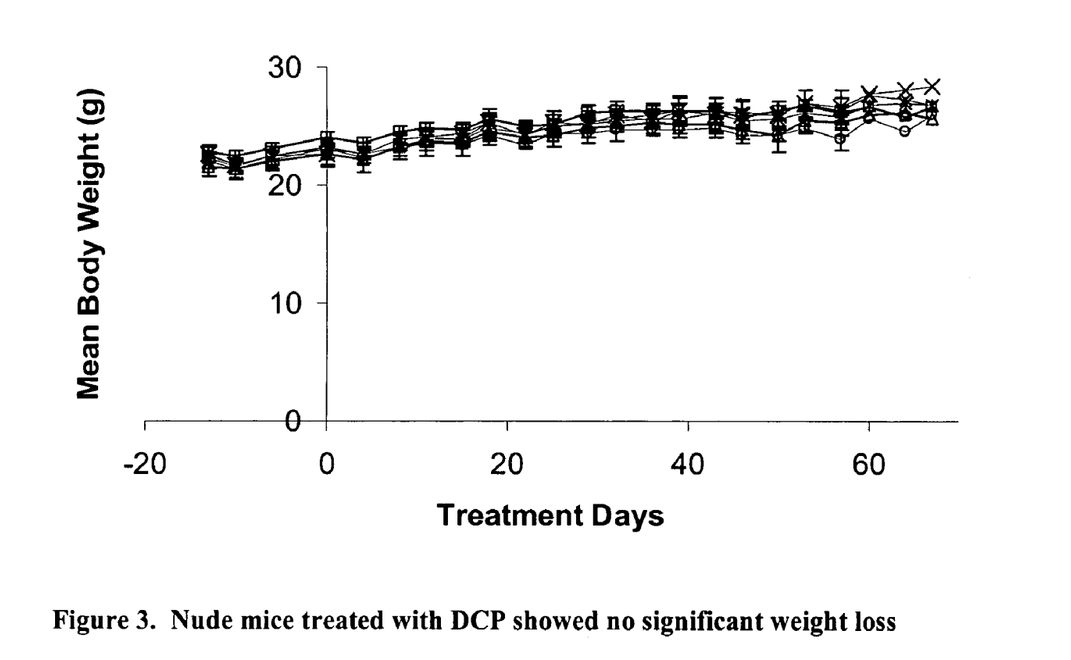
FIG. 3: Nude mice treated with DCP showed no significant weight loss.

There was no observed toxicity, as determined by body weight changes (see FIG. 3), among any of the groups of mice in this experiment.

FIG. 1 shows that the dipterinyl calcium pentahydrate (DCP) at 23 mg/kg/day has significantly greater anti tumor efficacy than the original CaPterin, (1:4 mol:mol) calcium pterin. DCP at 69 mg/kg/day, however, has comparable efficacy. Taken together, these findings imply that there appears to be an optimum dosage of DCP for maximal antitumor activity.

Conclusion: Our results show that oral dipterinyl calcium pentahydrate inhibits MDA-MB-231 xenograph tumors in nude mice significantly greater than (1:4 mol:mol) calcium pterin [CaPterin].

Figure 4:
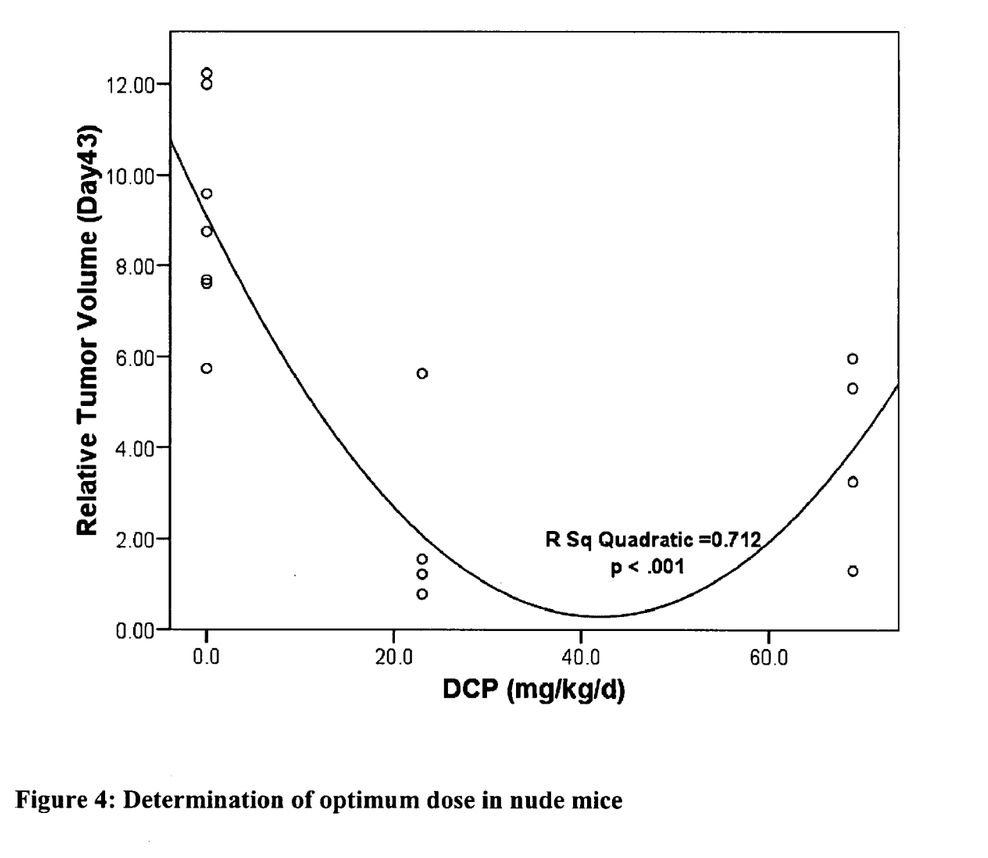
FIG. 4: Determination of optimum dose in nude mice.

Determination of the optimum dose in nude mice is shown in FIG. 4.

Figure 5:
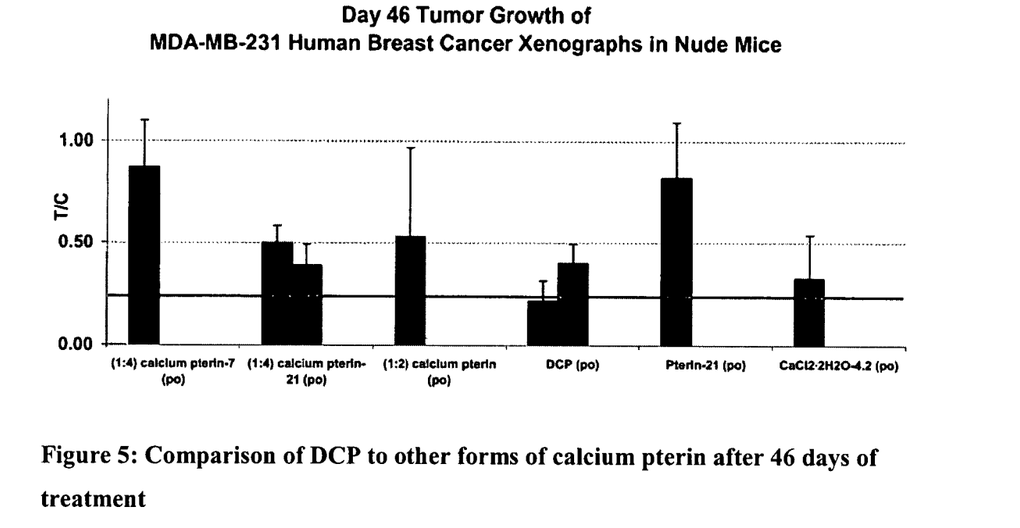
FIG. 5: Comparison of DCP to other forms of calcium pterin after 46 days of treatment.
Figure 6:
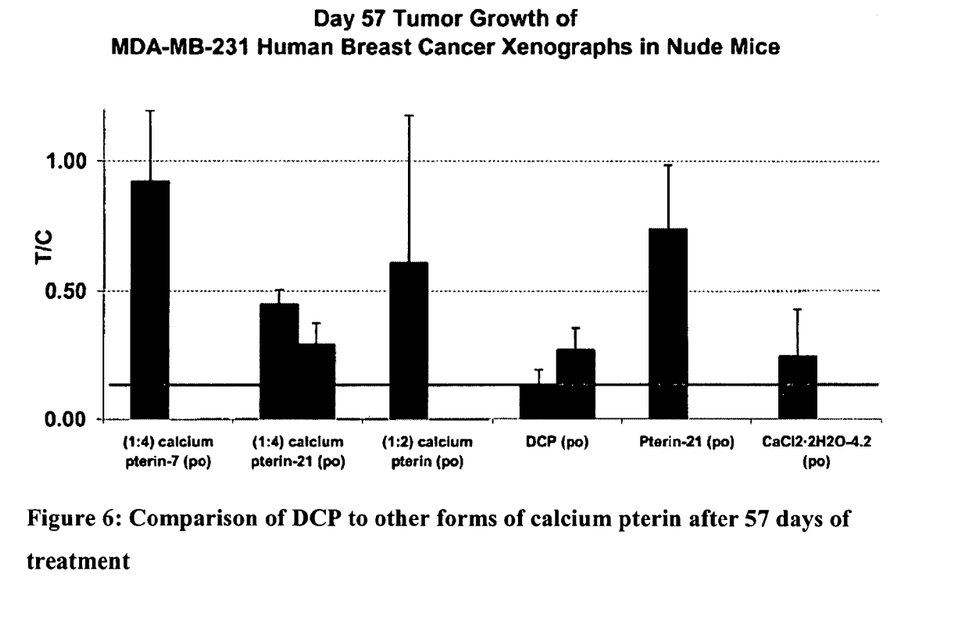
FIG. 6: Comparison of DCP to other forms of calcium pterin after 57 days of treatment.

Comparison of DCP to other forms of calcium pterin is shown in FIGS. 5 and 6.

Figure 7:
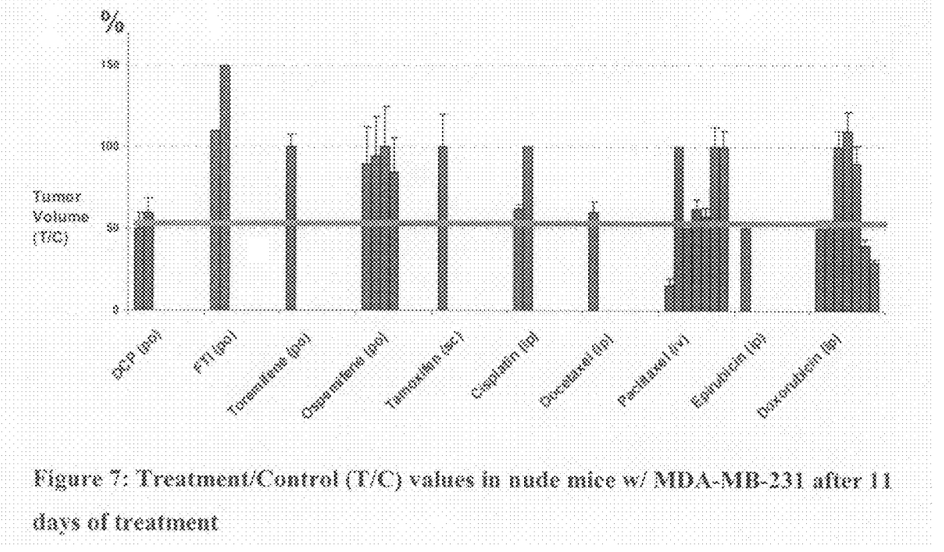
FIG. 7: Treatment/Control (T/C) values in nude mice w/MDA-MB-231 after 11 days of treatment.
Figure 8:
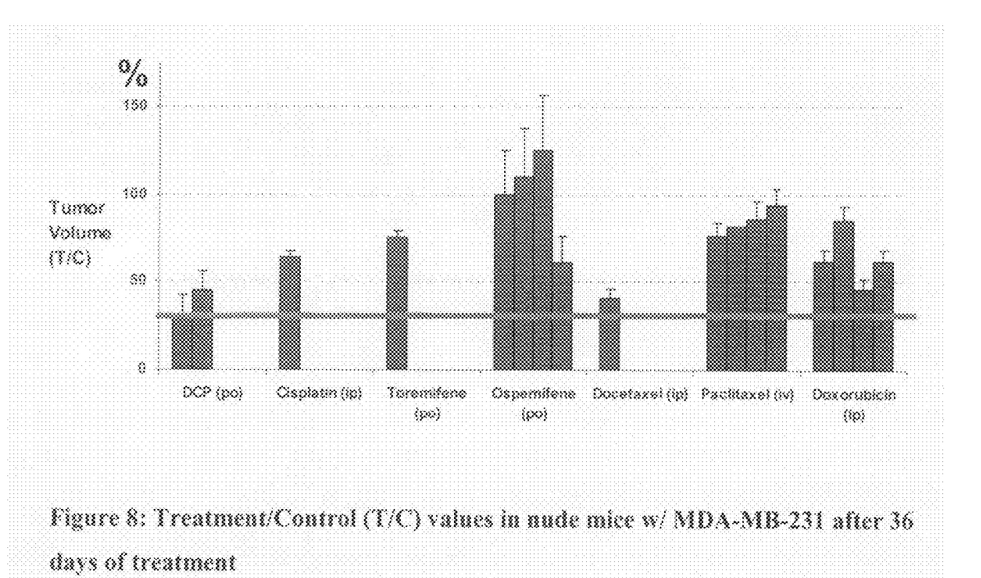
FIG. 8: Treatment/Control (T/C) values in nude mice w/MDA-MB-231 after 36 days of treatment
Figure 9:
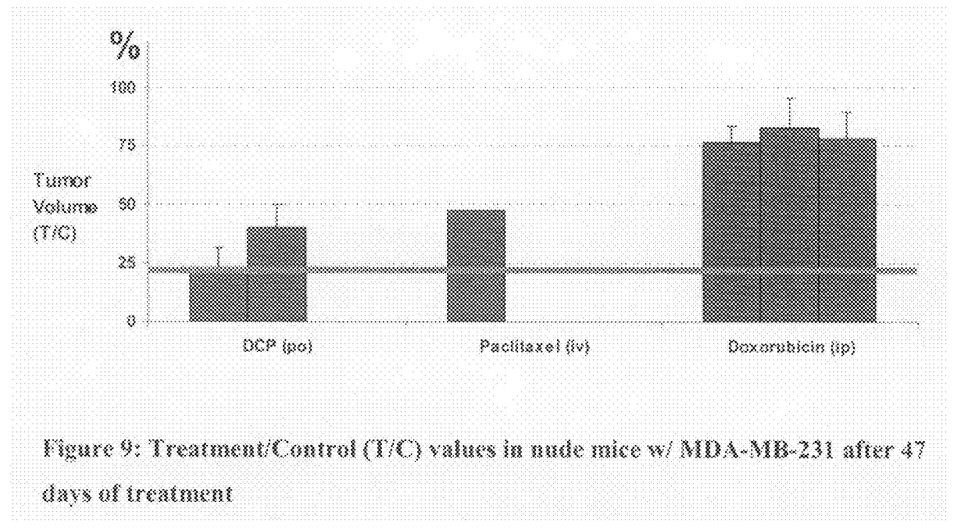
FIG. 9: Treatment/Control (T/C) values in nude mice w/MDA-MB-231 after 47 days of treatment

Comparison to other common chemotherapeutics is shown in the FIGS. 7, 8, and 9.

Comparative data for FIGS. 7, 8, and 9 was obtained from the following references:

Paclitaxel:

Milacic V, Chen D, Ronconi L, Landis-Piwowar KR, Fregona D, Dou Q P. A novel anticancer gold(III) dithiocarbamate compound inhibits the activity of a purified 20S proteasome and 26S proteasome in human breast cancer cell cultures and xenografts. Cancer Res. 2006 Nov. 1; 66(21): 10478-86.

LaMontagne K R, Butler J, Marshall D J, Tullai J, Gechtman Z, Hall C, Meshaw A, Farrell F X. Recombinant epoetins do not stimulate tumor growth in erythropoietin receptor-positive breast carcinoma models. Mol Cancer Ther. 2006 February; 5(2): 347-55.

Emi M, Kim R, Tanabe K, Uchida Y, Toge T. Targeted therapy against Bcl-2-related proteins in breast cancer cells. Breast Cancer Res. 2005; 7(6):R940-52. Epub 2005 Sep. 28.

Jones L W, Eves N D, Coumeya K S, Chiu B K, Baracos V E, Hanson J, Johnson L, Mackey J R. Effects of exercise training on antitumor efficacy of doxorubicin in MDA-MB-231 breast cancer xenografts. Clin Cancer Res. 2005 Sep. 15; 11(18):6695-8.

Yen W C, Lamph W W. The selective retinoid X receptor agonist bexarotene (LGD1069, Targretin) prevents and overcomes multidrug resistance in advanced breast carcinoma. Mol Cancer Ther. 2005 May; 4(5):824-34.

Han G Z, Liu Z J, Shimoi K, Zhu B T. Synergism between the anticancer actions of 2-methoxyestradiol and microtubule-disrupting agents in human breast cancer. Cancer Res. 2005 Jan. 15; 65(2):387-93.

Liao Y, Zou Y Y, Xia W Y, Hung M C. Enhanced paclitaxel cytotoxicity and prolonged animal survival rate by a non-viral-mediated systemic delivery of E1A gene in orthotopic xenograft human breast cancer. Cancer Gene Ther. 2004 September; 11(9):594-602.

Mewani R R, Tang W, Rahman A, Dritschilo A, Ahmad I, Kasid U N, Gokhale P C. Enhanced therapeutic effects of doxorubicin and paclitaxel in combination with liposome-entrapped ends-modified raf antisense oligonucleotide against human prostate, lung and breast tumor models. Int J Oncol. 2004 May; 24(5):1181-8.

FTI (Farnesyl Transferase Inhibitor):

Wamberg F, White D, Anderson E, Knox F, Clarke R B, Morris J, Bundred N J. Effect of a farnesyl transferase inhibitor (R115777) on ductal carcinoma in situ of the breast in a human xenograft model and on breast and ovarian cancer cell growth in vitro and in vivo. Breast Cancer Res. 2006; 8(2):R21. Epub 2006 Apr. 12.

Doxorubicin:

Emi M, Kim R, Tanabe K, Uchida Y, Toge T. Targeted therapy against Bcl-2-related proteins in breast cancer cells. Breast Cancer Res. 2005; 7(6):R940-52. Epub 2005 Sep. 28.

Hoke E M, Maylock C A, Shacter E. Desferal inhibits breast tumor growth and does not interfere with the tumoricidal activity of doxorubicin. Free Radic Biol Med. 2005 Aug. 1; 39(3):403-11. Epub 2005 Apr. 12.

Yen W C, Lamph W W. The selective retinoid X receptor agonist bexarotene (LGD1069, Targretin) prevents and overcomes multidrug resistance in advanced breast carcinoma. Mol Cancer Ther. 2005 May; 4(5):824-34.

Mewani R R, Tang W, Rahman A, Dritschilo A, Ahmad I, Kasid U N, Gokhale P C. Enhanced therapeutic effects of doxorubicin and paclitaxel in combination with liposome-entrapped ends-modified raf antisense oligonucleotide against human prostate, lung and breast tumor models. Int J Oncol. 2004 May; 24(5):1181-8.

Woessner R, An Z, Li X, Hoffman R M, Dix R, Bitonti A. Comparison of three approaches to doxorubicin therapy: free doxorubicin, liposomal doxorubicin, and beta-glucuronidase-activated prodrug (HMR 1826). Anticancer Res. 2000 July-August; 20(4):2289-96.

Docetaxel:

Emi M, Kim R, Tanabe K, Uchida Y, Toge T. Targeted therapy against Bcl-2-related proteins in breast cancer cells. Breast Cancer Res. 2005; 7(6):R940-52. Epub 2005 Sep. 28.

Sweeney C J, Mehrotra S, Sadaria M R, Kumar S, Shortle N H, Roman Y, Sheridan C, Campbell R A, Murry D J, Badve S, Nakshatri H. The sesquiterpene lactone parthenolide in combination with docetaxel reduces metastasis and improves survival in a xenograft model of breast cancer. Mol Cancer Ther. 2005 June; 4(6):1004-12.

Cisplatin:

Yen W C, Lamph W W. The selective retinoid X receptor agonist bexarotene (LGD1069, Targretin) prevents and overcomes multidrug resistance in advanced breast carcinoma. Mol Cancer Ther. 2005 May; 4(5):824-34.

Epirubicin:

Yamamoto D, Tanaka K, Nakai K, Baden T, Inoue K, Yamamoto C, Takemoto H, Kamato K, Hirata H, Morikawa S, Inubushi T, Hioki K. Synergistic effects induced by cycloprodigiosin hydrochloride and epirubicin on human breast cancer cells. Breast Cancer Res Treat. 2002 March; 72(1): 1-10.

Ospemifene:

Taras T L, Wurz G T, DeGregorio M W. In vitro and in vivo biologic effects of Ospemifene (FC-1271a) in breast cancer. J Steroid Biochem Mol Biol. 2001 June; 77(4-5):271-9.

Tamoxifen:

Cameron D A, Ritchie A A, Langdon S, Anderson T J, Miller W R. Tamoxifen induced apoptosis in ZR-75 breast cancer xenografts antedates tumour regression. Breast Cancer Res Treat. 1997 September; 45(2):99-107.

Jordan V C, Gottardis M M, Robinson S P, Friedl A. Immune-deficient animals to study "hormone-dependent" breast and endometrial cancer. J Steroid Biochem. 1989; 34(1-6): 169-76.

Toremifene:

Robinson S P, Parker C J, Jordan V C. Preclinical studies with toremifene as an antitumor agent. Breast Cancer Res Treat. 1990 August; 16 Suppl:S9-17. Review.

Robinson S P, Jordan V C. Antiestrogenic action of toremifene on hormone-dependent, -independent, and heterogeneous breast tumor growth in the athymic mouse. Cancer Res. 1989 Apr. 1; 49(7):1758-62.

What is claimed is:

1. The compound dipterinyl calcium pentahydrate (DCP).

2. A method of synthesizing dipterinyl calcium pentahydrate (DCP) comprising:
dissolving pterin in an aqueous solution of NaOH,
adding $CaCl_2.2H_2O$ to the solution with stirring at a pH of about 11,
continuing stirring for about 1 day, and
collecting the precipitate as DCP.

3. A pharmaceutical composition comprising a pharmaceutically acceptable excipient and the compound dipterinyl calcium pentahydrate (DCP).

* * * * *